(12) United States Patent
Douglas

(10) Patent No.: US 6,544,474 B2
(45) Date of Patent: Apr. 8, 2003

(54) DEVICE FOR DETERMINATION OF AN ANALYTE IN A BODY FLUID USING SMALL SAMPLE SIZES

(75) Inventor: Joel S. Douglas, Los Altos Hills, CA (US)

(73) Assignee: Amira Medical, Scotts Valley, CA (US)

( * ) Notice: Subject to any disclaimer, the term of this patent is extended or adjusted under 35 U.S.C. 154(b) by 0 days.

(21) Appl. No.: 09/755,362

(22) Filed: Jan. 5, 2001

(65) Prior Publication Data

US 2001/0001034 A1 May 10, 2001

Related U.S. Application Data

(63) Continuation of application No. 09/164,212, filed on Sep. 30, 1998, now abandoned.
(60) Provisional application No. 60/060,458, filed on Sep. 30, 1997.

(51) Int. Cl.$^7$ ........................ G01N 21/01; C12M 1/34; C12M 1/40; B32B 23/00
(52) U.S. Cl. ...................... 422/56; 422/57; 422/58; 422/82.05; 435/287.7; 435/287.9; 435/288.7
(58) Field of Search .............. 435/7.1, 287.1, 435/287.6, 287.7, 287.8, 288.1, 288.7, 287.9; 436/169; 422/56, 58, 82.05, 57; 356/929

(56) References Cited

U.S. PATENT DOCUMENTS 5,387,526 A  *  2/1995  Garner et al.
5,968,839 A  *  10/1999  Blatt et al. .................. 436/513

* cited by examiner

Primary Examiner—John S. Brusca
Assistant Examiner—Marjorie A. Moran
(74) Attorney, Agent, or Firm—Woodard, Emhardt, Naughton, Moriarty & McNett LLP

(57) ABSTRACT

Devices and methods for utilizing dry chemistry dye indicator systems for body fluid analysis such as glucose level in whole blood are provided by incorporating an indicator in a bibulous matrix contained inside a hollow fiber capillary tube adapted to wick the fluid sample into the tube to wet the matrix and indicator system. The devices also enable visual or meter reading of the indicator by positioning the hollow fiber capillary tube in a housing having an optical opening adapted for receiving light form a source and directing the light to the capillary tube and for directing the light reflected therefrom to a detector. An advantage for the individual user is the small fluid, e.g., blood sample required, which enables the user to avoid using finger tip sticks for samples. Another aspect of the device provides a determination of and correction for hematocrit level in whole blood in combination with indicator indication of analyte concentration. The devices provided are low cost due to efficient manufacturing.

7 Claims, 2 Drawing Sheets

DEVICE FOR DETERMINATION OF AN ANALYTE IN A BODY FLUID USING SMALL SAMPLE SIZES application is continuation, divisional, of application Ser. No. 09/164,212, filed Sep. 30, 1998, now abandoned, which claims benefit of 60/060/458, filed Sep. 30, 1997.

FIELD OF THE INVENTION

The present invention relates to a test device and determination of a chemical or biochemical component (analyte) in an aqueous body fluid, such as whole blood or interstitial fluid. In particular the present invention relates to a dry reagent test device from which an analyte presence and/or concentration is determined by use of an instrument and a disposable capillary reagent carrier and acquisition device. A common use of such test devices is for determination of glucose level in blood by diabetics.

BACKGROUND OF THE INVENTION

Numerous devices have been developed to test for presence and quantity of analytes in aqueous samples, such as whole blood or urine. The patent and technical literature of the last years is replete with inventions which utilize a reagent strip containing a dry chemistry reagent system, that is, a system in which the wet chemistries are imbibed into an absorbent or bibulous medium, dried, and later reconstituted by fluid from the test sample. The reagent strips contain an indicator which changes color, depending on the presence or concentration of a particular analyte in a biological fluid applied to the strip. These strips may be read visually by reference to a color standard or colorimetrically by instrument calibrated or programmed to detect a certain color. Although some of these strips use reduction chemistries, more commonly they involve an oxidizable dye or dye couple. Some of the strips include an enzyme, such as glucose oxidase, which is capable of oxidizing glucose to gluconic acid and hydrogen peroxide. They also contain an oxidizable dye and a substance having peroxidative activity, which is capable of selectively catalyzing oxidation of the oxidizable dye in the presence of hydrogen peroxide. (See, for example, U.S. Pat. No. 4,935,346, to Phillips et al.) Examples of these devices, in addition to those used to test blood glucose, include tests for cholesterol, triglycerides, calcium or albumin in whole blood, and for protein, ketones, albumin or glucose in urine.

Dry chemist reagent strips incorporating enzyme-based compositions are used daily by millions of diabetics to determine blood glucose concentrations. The NIH sponsored study, the Diabetes Complications and Control Trial, demonstrated conclusively that careful control of blood glucose levels can significantly reduce the incidence of serious complications of diabetes such as vision loss and kidney malfunction. Most diabetics must test themselves periodically in order to make appropriate adjustments to their diet or medication. It is thus especially important for diabetics to have rapid, inexpensive, and accurate reagent strips for glucose determination. The embodiment of dry chemistry reagent systems in test strips enable simple yet effective analytical protocols.

The technologies embodied in the products which have been developed to date have certain limitations from the perspective of the end user and/or the manufacturer. There is, therefore, a need to overcome some of the limitations of currently available testing systems. U.S. Pat. No. 3,092,465, issued to Adams et al., U.S. Pat. No. 3,298,789, issued to Mast and U.S. Pat. No. 3,630,957, issued to Rey et al., all describe a basic reagent system which became a standard for colorimetric determination of glucose in biological samples. These patents describe the formation of a film layer or semi-permeable coating over the bibulous matrix to hold back the larger particulates, such as red blood cells, and allow fluid to permeate into the bibulous matrix. This approach requires the removal of red blood cells by washing or wiping to enable visual inspection or instrument reading of the indication of the dye color formed in the matrix.

Stone, U.S. Pat. No. 3,607,093, discloses a membrane for testing blood where the membrane has a skin permeable to solutions but impermeable to solids such as red blood cells and to macromolecules such as proteins. This membrane is disclosed as being used by applying a blood sample then wiping away the red blood cells from the skin in order to reach the test indication through the skin.

U.S. Pat. 3,552,928, issued to Fetter discloses the use of certain water soluble salts and amino acids in reagent formulations as separation agents to provide blood separation. With solids such as red blood cells substantially removed from the biological fluid, there is less background color at the test site to obscure a change in coloration produced by a testing reagent.

Phillips et al., U.S. Pat. No. 4,935,346 discloses a system wherein a whole blood sample is applied to the device and indicator development occurs in the presence of the colored components of the sample. Measurements of the color change in indicator are made at two distinct wavelengths to eliminate the interferences from the presence of colored blood components.

Terminello et al., U.S. Pat. No. 4,774,192, disclose a system in which the matrix is formed of an asymmetric material used to filter the red blood cells in the sample. The asymmetric material has a density gradient from one side to the other to progressively separate red blood cells from the fluids.

Erikson, et al., U.S. Pat. No. 5,582,184 disclose a system which uses a small capillary tube, membrane, and infrared testing.

Daffern et al., U.S. Pat. No. 4,994,238, disclose a test device that comprises an asymmetric reagent layer that has progressively finer filtration with increased distance from one surface toward the other surface.

Castino et al., U.S. Patent No. 5,456,835 disclose the use of filters formed of ligand modified polymeric film such as polypropylene fibers and polyethersulfone fibers.

Vogel et. al., U.S. Pat. No. 4,477,575, disclose the use of glass fiber material to achieve blood separation through the thickness of the material. Blood is applied to one side of the glass fiber, and relatively clear fluid migrates out of the opposite side. This fluid is delivered to an additional layer where the detection of analytes can occur.

Macho et al., U.S. Pat. No. 5,451,350, disclose the use of absorbent channels to distribute sample fluid in multi-zone test devices. Charlton et al., U.S. Pat. No. 5,208,163, also disclose the use of capillary channels to distribute blood to various chambers in the device.

Pending U.S. patent application Ser. No. 08/628,489 (published as PCT International Publication No. WO 97/38126) describes the use of microporus material and the concept of microtitration which are well suited for this application.

Ash et al., U.S. Pat. Nos. 4,854,322 and 4,77,953 disclose a capillary filtration and collection device for long term monitoring of blood constituents which is implanted within the interstitial body space in fluid communication with blood capillaries.

The disclosures of the above patents are incorporated herein by reference.

The prior art devices and methods of the above references provide varying degrees of effectiveness of blood analysis at varying degrees of complexity and cost.

It is an object of the present invention to provide improved devices and methods to improve the performance and minimize the cost and complexity compared to the prior art devices.

It is a further object of the present invention to provide a fully disposable, discrete reading system for detecting an analytes presence or concentration.

It is another object of this invention to provide capillary format for testing which provides an easy to use, low volume device which is easy to manufacture.

It is another object of this invention to provide capillary format for testing which permits the patient to use non traditional body locations to extract a sample of body fluids.

It is another object of this invention to provide a means for measuring low volume body fluids such as interstitial fluid.

It is still a further object of this invention to provide a dry chemistry reagent and test strip which can be used in an electronic meter to analyze body fluids for one or more analytes.

The above objects as well as others are achieved by the devices, methods and systems of this invention as disclosed herein.

SUMMARY OF THE INVENTION

In one aspect this invention provides a method of testing or analyzing body fluids for the presence or concentration of an analyte by using a porous matrix. The porous matrix is provide through the use of hollow fiber made from various polymers including polyethersulphone, polysulphone, polyurethane, and other hydrophilic polymers. The hollow fibers can be dual skin in that they have two skins; one on the inner diameter and one on the outer diameter with various pore structures connecting the two skins, or have a single inner diameter skin with an isotropic pore structure radiating outward. The pore size of these skins can be either similar or dissimilar, but preferably should not be less than 0.1 microns and less that 5 microns in size.

In a preferred embodiment of the invention the device comprises of a capillary system which is used to collect the sample of body fluid. The capillary is the hollow portion of the hollow fiber. The sample is wicked up the hollow fiber and wets out the fiber matrix which is used as the membrane for analysis. The use of a hollow fiber capillary tube to collect the sample permits the patient the ability to collect a very small sample from any body location thereby increasing the number of possible sampling sites and body fluids where the patient can extract a sample of body fluid. The apparatus comprises of a hydrophilic hollow fiber capillary. The matrix can then be tested using various techniques including infrared, electrochemical, or colormetric means. When using the matrix which forms the hollow fiber matrix for electrochemical or colormetric analysis, it is imbibed with indicator capable of indicating the presence or concentration of the analyte. The hollow fiber capillary can be cast from a hydrophilic compound, or hydrophilic agents can be coated either prior to or during reagent application.

The test method comprises applying a blood sample to the hollow fiber capillary by placing the hollow fiber capillary tube in communication with the sample and, allowing it to wick up the tube and wet out the matrix of the hollow fiber. This permits the fluid to pass through the hollow fiber capillary spreading onto the matrix. The reading or measuring for the presence/concentration of the analyte being tested is accomplished by detecting the change in reflectance of the indicator reagent for a colormetric test which is imbibed into the matrix.

The embodiments of the devices of the invention with the appropriate dry chemistry system in the matrix member can be used in test strips which may be read or measured in an electronic meter.

The above sets forth the generic aspects of the device and methods of the present invention. These device and methods are more fully described in the drawings and the descriptions below.

DETAILED DESCRIPTION OF THE INVENTION

Figure 1:
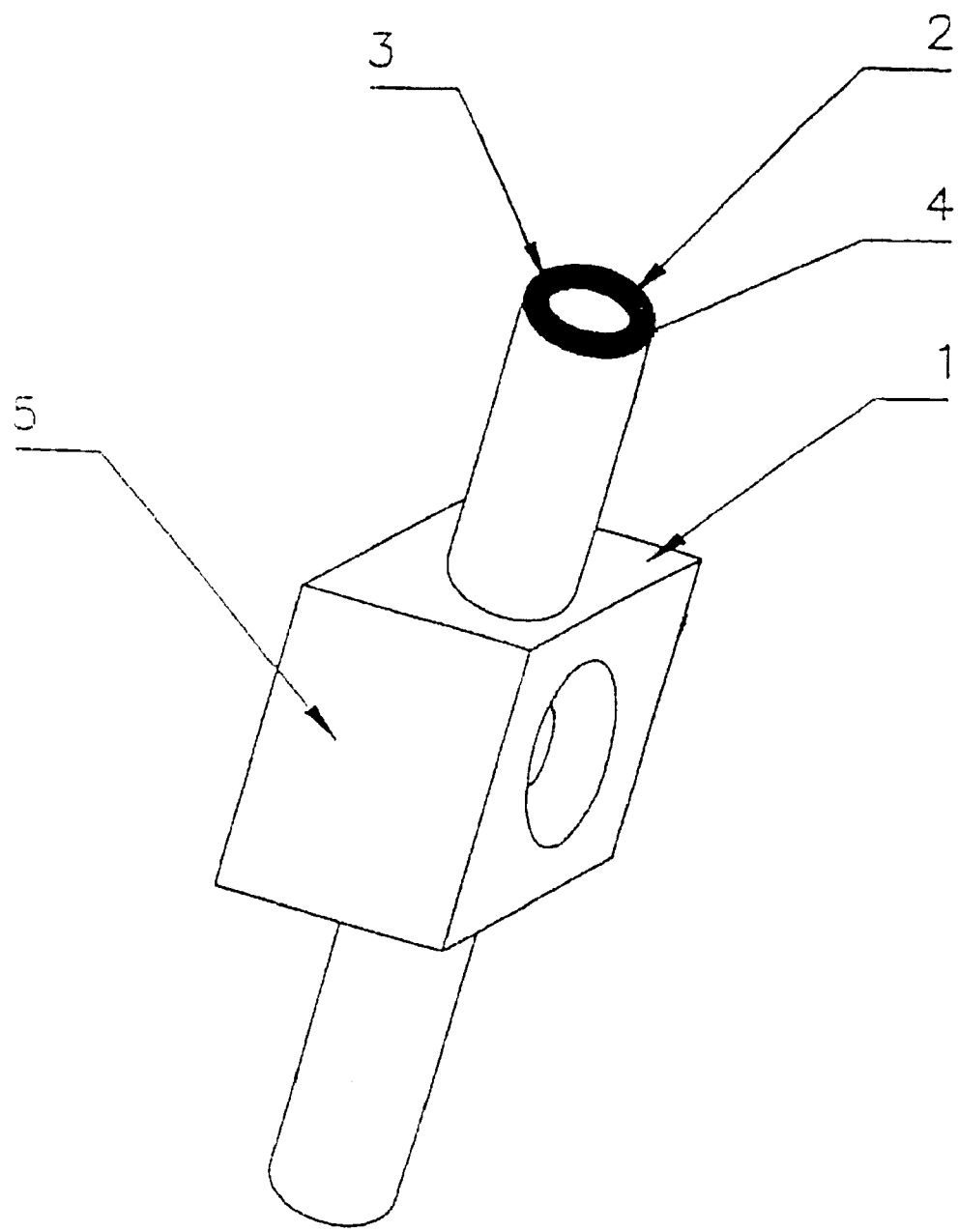
FIG. 1 is an isometric view of the hollow fiber capillary test device

The devices of the present invention are simpler to use and are easier and less costly to manufacture than most devices previously available. This is especially important for diabetics who rely on blood glucose testing multiple times per day to keep their disease under control. For many diabetics, the costs associated with blood glucose monitoring are significant, especially elderly diabetics on fixed incomes. Devices of various configurations and various uses based on the embodiments of the invention disclosed herein can be delivered to the diabetic patient, in a more cost effective manner. The ease of use and ability to capture the sample provide a means to use non traditional sites to extract a sample. This eliminates the need for the patient to continually use the finger tips as a sampling site. The convenience of these devices, coupled with more attractive pricing, will facilitate increased patient compliance with recommended testing routines and will result in improved overall health of diabetic patients.

As used herein, reference is primarily made to blood. However, other fluids such as urine, saliva, interstitial fluid and the like can be analyzed utilizing the various embodiments of the present invention. The hollow fiber capillary matrix used in the invention are preferably a polyethersulfone polymer which is cast to inherently have a microporous skin on one side and a porous matrix on the other side, such as the Gelman membrane. However, one may also employ a matrix of polysulphone, polyurethane, and other hydrophilic polymers, as well as hydrophobic polymers that are compatible with hydrophilic castings or surface treatments.

The dry chemistry components useful in this invention are illustrated by the embodiments which follow in the disclosure herein. Additional dry chemistry components useful in this invention are described in the disclosures in copending U.S. patent application Serial No. 08/628,489 filed Apr. 5, 1996 and U.S. Pat. No. 5,776,719, the disclosures of which are incorporated herein by reference in their entirety.

In this invention, the preferred method for providing a test area geometry is to utilize a hollow fiber as the capillary wick and reagent bearing member. The sample entry to the membrane test area which is the matrix of the hollow fiber is via the capillary center portion of the hollow fiber. The sample is wicked up the hollow fiber and wets out the surrounding matrix. The sample wets out the dried reagent imbibed in the matrix and the analyte reacts with the detection reagent to indicate the presence and/or concentration of the analyte. If used with an infrared detection system, the matrix does not contain an indicating chemistry.

Hollow fibers are known in other applications. For example, see Schoonen et al., U.S. Pat Nos. 5,615,671 and 5,174,291, the disclosures of which are incorporated herein by reference.

A wetting agent may be imbibed into the matrix of the hollow fiber to increase the hydrophilic properties of the hollow fiber to facilitate body fluid flow into the capillary tube and the matrix. High molecular weight polymeric oils work well as wetting agents. A preferred material is dimethylsiloxane ethylene oxide, part number PS073 from United Chemical Technologies. Other wetting agents include polypropylene glycol or polyethylene glycol.

Separating agents can be impregnated into the matrix during or after the impregnation of test reagents. The specific compounds are selected to enhance the ability of the matrix to separate whole blood into red blood cells and clear fluid. As discussed previously, the preferred matrix materials comprise a microporous polyethersulfone.

The separating agents which can be impregnated into the membrane and or capillary wick may be selected from the following: polyvinyl sulfonic acid (PVSA), polyethylene glycol (PEG), polystyrene sulfonic acid (PSSA), hydroxypropyl cellulose (commercially available as Klucel ™), polyvinyl alcohol (PVA), polyvinylpyrrolidone (PVP), polyacrylic acid (PAA), water soluble salts, citrates, formates and sulfates, amino acids, chitosan(amino sugar), dextrans, citric acid, phytic acid and malic acid. These materials may be enhanced through combining with silica or clay. The chemical components can include equivalent materials which help to separate whole blood into red blood cells and relatively clear fluid.

The indicating reagent mix must be capable of detecting the presence of the analyte. In general, the analyte reacts with a specific oxidase enzyme and produces hydrogen peroxide. This strongly oxidative substance reacts with the indicator(s) present to produce a colored end product. The oxidase enzyme may be one of the following: glucose oxidase, cholesterol oxidase, uricase, alcohol oxidase, aldehyde oxidase or glycerophosphate oxidase. While the examples and preferred embodiments herein comprise glucose oxidase in the formulations, formulation changes required to utilize other oxidase enzymes are evident to one who is skilled in the art. The indicator chemistries which provide acceptable color generation when coated on the hollow fiber matrix (polyethersulfone) may be chosen from 3-methyl-2-benzothiazolinone hydrazone hydrachloride (MBTH) combined with 3,3-dimethylaminobenzoic acid (DMAB), MBTH combined with 3,5-dichloro-2-hydroxybenzene-sulfonic acid (DCHBS); 4-aminoantipyrene (4-AAP) and 5-Oxo-1-(p-sulfophenyl)-2-pyrazoline-3-carboxylic acid(OPSP); 4-AAP and n-(m-tolyl)-diethanolamine (NDA); 2,2'-azino-di(3-ethylberhthiazoline) sulfonic acid (ABTS); 4AAP and 4-methoxynaphthol; pyrogallol red(PGR); bromopyrogallol red (BPR); acid green 25 (AG); MBTH and 8-anilino-1-naphthalenesulfonate (ANS); or N-(3-sulfopropyl)aniline and MBTH; or other known and conventional dye system for different analytes. U.S. Pat. No. 5,306,623 to Kiser et. al. discloses effective concentrations of a number of useful dye systems.

The MBTH-ANS system described by Yu in U.S. Pat. No. 5,453,360 may be used in the methods and devices of this invention. One who is skilled in the art can formulate an acceptable chemistry based on the components disclosed herein and in the prior art.

The above reagents will create a chemistry which can be read with a meter. The separation reagents, indicator reagents, oxidase enzymes, peroxidase enzymes, hematocrit adjuster, buffers, and chelators together with the dye system are impregnated in a membrane matrix selected from polyethersulfone.

The issue of hematocrit level affecting the accuracy of test results is a substantial one for a test device. The following embodiment of this invention can be used to compensate for the hematocrit variation of whole blood. The instrument can be designed with additional sensors. These can either be electrical contacts or light sources and receivers (sensors) connected to analog signaling/conditioning circuit. These additional sensors can be implemented so that they inspect the capillary in the hollow fiber, one sensor at the beginning of the channel and one at the end. Whole blood is applied to the capillary. The test device capillary is translucent when using light sensors and the movement of whole blood is timed between sensors. The time that the blood takes to travel up the capillary is an indication of the hematocrit of the blood, and that information is used to correct any shift in reflectance readings of the instrument caused by the hematocrit level.

In The various aspects of the invention disclosed herein can best be illustrated by reference to the drawings and the description thereof which follows.

The hollow fiber capillary test device 1 is shown in FIG. 1. The hollow core 2 of the fiber acts as a capillary. The second component is the matrix 3 or filtering media which contains the dried indicating reagent 4. This hollow fiber sits in an injected molded housing, preferably having an optical cavity housing 5 which provides the structural support for the hollow fiber.

Figure 2:
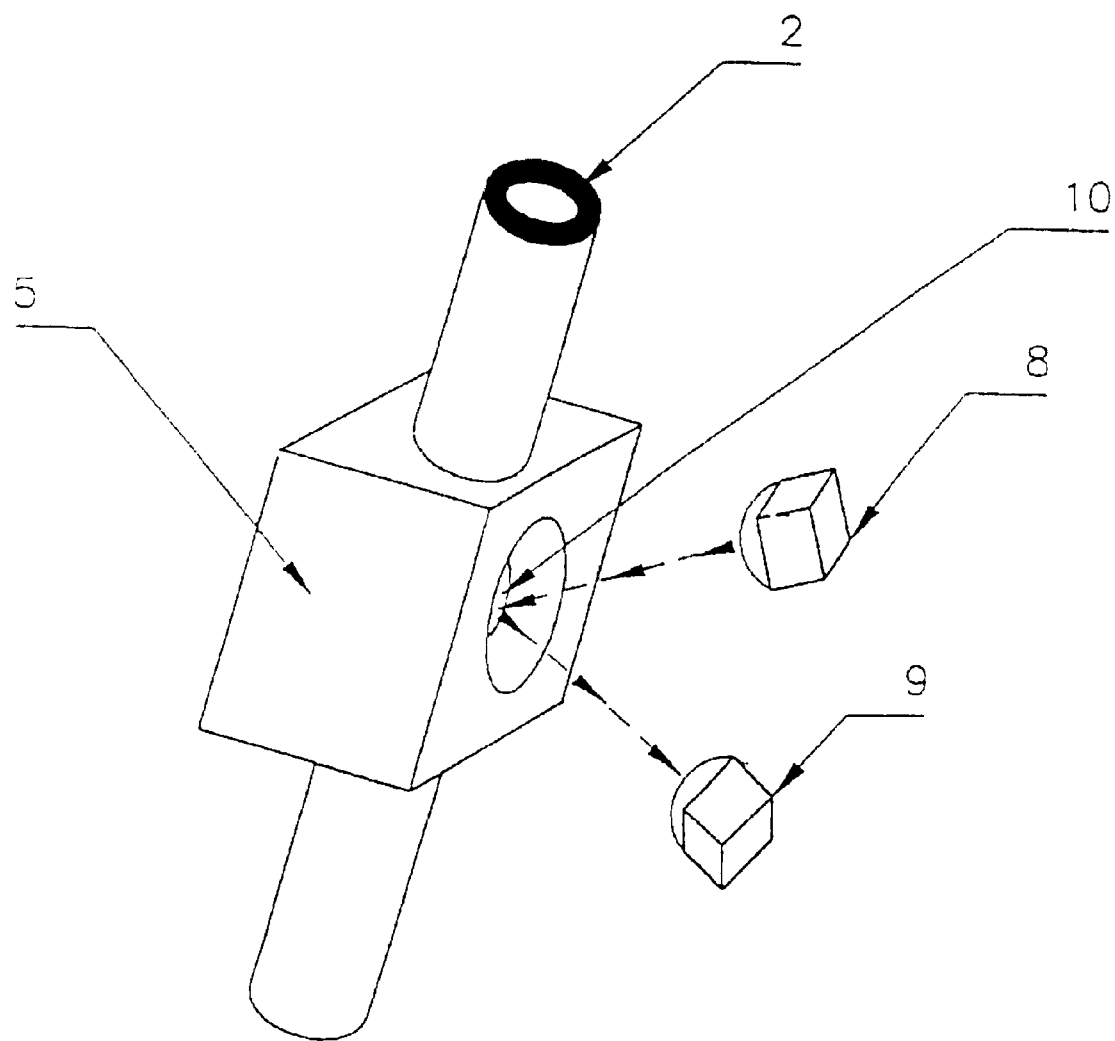
FIG. 2 is an isometric view of the hollow fiber capillary device being read by a reflectance meter.

FIG. 2 shows the device described in FIG. 1 in which the indicating reagent is in the reacted state after absorbing the sample. The LED 8 and photo detector 9 read the color change through the hole 10 in injection molded part 5. For the purpose of obtaining the best optical positioning, the molded optical cavity housing can be designed to focus light from an LED onto the hollow fiber, or focus light emitted from the hollow fiber onto a detector, such as a photo diode detector. To correct for losses of efficiencies due to variables such as the size and position of the fiber, position of the detector, and optical efficiency of the system, a two LED system can be utilized. One LED system can be selected to monitor the intensity of a dye impregnated into the fiber with the chemistry, while the other LED would monitor the color produced by the analyte of interest. The two wave length system of Phillips, et al., U.S. Pat. No. 4,935,346 could also be used to correct for hemoglobin or blood, in the case where whole blood is the sample.

The matrix material 3 will generally be in the ranges of about 0.1 microns to 5 microns in pore size. It will be recognized by those skilled in the art that the inside diameter of the fiber, the thickness of the matrix and the reagent used according to this invention may vary according to the desired use.

The devices of this invention are conveniently made into test devices of convenient size and configuration for use in instruments or meters which are adapted to measure the color or other indication provided by the device. They are extremely useful for creating test devices which use small sample volumes. The complete sample is used by the device in that the fluid wicked up the hollow fiber is absorbed by the surrounding matrix and the indicating reaction takes place in this matrix.

The following is an example of making and using the devices of this invention for the most preferred embodiment.

EXAMPLES

Glucose Test

Example A

Test Reagents

| Reagent 1a | 40 mg MBTH-S |
| | 80 mg DMAB |
| | 5 ml acetonitrile and 5 ml water |
| | Stir until all solids are dissolved. |
| Reagent 2a | 6 ml water |
| | 10 mg EDTA, disodium salt |
| | 200 mg PolyPep, low viscosity (Sigma) |
| | 0.668 g sodium citrate |
| | 0.523 g citric acid as a hematocrit adjuster |
| | 0.2 M Aconitic acid buffer |
| | 3% polyethylene glycol (PEG), as a separating agent |
| | 0.5% Polyquart, a binder |
| | 2.0 ml 6 wt % Gantrez AN-139 dissolved in water (GAF) |
| | 30 mg horseradish peroxidase, 100 units/mg, and |
| | 3.0 mg glucose oxidase, 2000 units/ml |
| | Stir until dissolved. |

Example B

Test Reagents

| Reagent 1b | 20 ml water |
| | 420 mg citric acid (a buffering agent). |
| | Adjust the pH of the citric acid |
| | solution with NaOH to a value of 4.25. |
| | 16.7 mg EDTA |
| | 90 mg Gantrez S95 available from GAF |
| | 250 mg Crotein SPA |
| | 20,500 units glucose oxidase |
| | 16,200 units peroxidase |
| Reagent 2b | 10 ml of a mixture of 3 parts by volume water and |
| | 7 parts by volume isopropyl alcohol |
| | 13 mg MBTH-S |
| | 40 mg ANS |

Test A

Polyethersulfone Hollow Fiber Matrix

A piece of polyethersulfone hollow fiber is imbibed with reagent 1a; and the material is dried. The hollow fiber is then coated with reagent 2a in the same fashion and dried. The hollow fiber is then assembled into a test device as shown in FIG. 1. Whole blood is applied to the capillary opening and the glucose level is read from side wall of the hollow fiber based on the indicator response in the test zone.

What is claimed is:

1. A device for testing a body fluid for concentration of an analyte, said device comprising:
    a hollow fiber capillary tube, said hollow fiber capillary tube comprising a tube wall defining a hollow core, said tube wall comprising a matrix for receiving a fluid sample;
    an indicating reagent contained in said matrix for reacting with an analyte to provide indication of the concentration of the analyte; and
    a housing in which the hollow fiber capillary tube is positioned, said housing having an opening adapted for receiving light from a light source and for directing light reflected from the hollow fiber capillary tube to a light detector.

2. A device according to claim 1 wherein the capillary tube inside diameter is between 0.001 inches and 0.100 inches.

3. A device according to claim 1 wherein the capillary tube is formed from a hydrophilic polymer or a hydrophobic polymer coated or treated with a hydrophilic surface treating agent.

4. A device according to claim 3 wherein the polymer comprises polyethersulphone, polysulphone, polyyrethane, nylon, nitrocellulose, polyethylene, polytetrafluoroethylene, halogenated vinyl polymers or cellulose derivatives.

5. A device according to claim 1 wherein the housing opening comprises an optical cavity adapted to optimize the alignment of the hollow fiber capillary tube with the light source and detector.

6. A device according to claim 1 in combination with a meter comprising a light source and a light detector positioned to provide light to and receive reflected light from the hollow fiber capillary tube positioned in the opening of the housing.

7. A method for determining the concentration of an analyte in a body fluid, said method comprising:
    (a) providing a device comprising:
        a hollow fiber capillary tube, said hollow fiber capillary tube comprising a tube wall defining a hollow core, said tube wall comprising a matrix for receiving a fluid sample;
        an indicating reagent contained in the matrix for reacting with the analyte to provide indication of the concentration of the analyte; and
        a housing in which the hollow fiber capillary tube is positioned, said housing having an opening adapted for receiving light from a light source and for directing light reflected from the hollow fiber capillary tube to a light detector;
    (b) contacting the hollow fiber capillary tube with a sample of body fluid to allow the sample to wick into the tube thereby wetting the matrix and indicator; and
    (c) measuring a color change of the indicator and determining the concentration of the analyte in the sample.

* * * * *

UNITED STATES PATENT AND TRADEMARK OFFICE
CERTIFICATE OF CORRECTION

PATENT NO. : 6,544,474 B2
DATED : April 8, 2003
INVENTOR(S) : Douglas

It is certified that error appears in the above-identified patent and that said Letters Patent is hereby corrected as shown below:

<u>Title page,</u>
Item [57], ABSTRACT,
Line 9, replace "light form a source" with -- light from a source --.

<u>Column 1,</u>
Line 48, replace "chemist" with -- chemistry --.

<u>Column 8,</u>
Line 25, replace "polyyrethane," with -- polyurethane, --.

Signed and Sealed this

Eighth Day of June, 2004

JON W. DUDAS
*Acting Director of the United States Patent and Trademark Office*